United States Patent
Ullrich et al.

(10) Patent No.: US 9,881,520 B2
(45) Date of Patent: Jan. 30, 2018

(54) VIRTUAL TOOL MANIPULATION SYSTEM

(75) Inventors: Christopher J. Ullrich, Santa Cruz, CA (US); Kevin J. Kunkler, Frederick, MD (US)

(73) Assignee: Immersion Medical, Inc., Gaithersburg, MD (US)

( * ) Notice: Subject to any disclaimer, the term of this patent is extended or adjusted under 35 U.S.C. 154(b) by 930 days.

(21) Appl. No.: 11/970,625

(22) Filed: Jan. 8, 2008

(65) Prior Publication Data
US 2009/0177452 A1     Jul. 9, 2009

(51) Int. Cl.
| | |
|---|---|
| G06G 7/60 | (2006.01) |
| G09B 23/30 | (2006.01) |
| G09B 23/28 | (2006.01) |
| G06F 3/01 | (2006.01) |
| A61B 34/00 | (2016.01) |
| A61B 34/20 | (2016.01) |

(52) U.S. Cl.
CPC .............. *G09B 23/28* (2013.01); *A61B 34/74* (2016.02); *A61B 34/76* (2016.02); *G06F 3/014* (2013.01); *G06F 3/016* (2013.01); *G09B 23/285* (2013.01); *A61B 34/20* (2016.02); *A61B 2034/741* (2016.02)

(58) Field of Classification Search
CPC ....... G09B 23/28; G09B 23/285; G06F 3/014; G06F 3/016; A61B 2019/2269; A61B 2019/2273; A61B 2019/2292
USPC ........ 600/595, 407, 427, 429, 587; 345/156, 345/184; 318/566; 703/11; 434/267
See application file for complete search history.

(56) References Cited

U.S. PATENT DOCUMENTS

| | | | | |
|---|---|---|---|---|
| 4,907,973 | A | * | 3/1990 | Hon ............................ 434/262 |
| 4,988,981 | A | * | 1/1991 | Zimmerman et al. ........ 345/158 |
| 5,143,505 | A | | 9/1992 | Burdea |
| 5,800,179 | A | * | 9/1998 | Bailey .......................... 434/262 |
| 5,828,197 | A | * | 10/1998 | Martin et al. ................. 318/567 |
| 5,855,553 | A | | 1/1999 | Tajima et al. |
| 6,113,395 | A | | 9/2000 | Hon |

(Continued)

FOREIGN PATENT DOCUMENTS

| | | |
|---|---|---|
| JP | 7-44312 A | 2/1995 |
| JP | 11-195140 A | 7/1999 |

(Continued)

OTHER PUBLICATIONS

Menciassi et al.; "Force Feedback-Based Microinstrument for Measuring Tissue Properties and Pulse in Microsurgery"; Proceedings of the 2001 IEEE; International Conference on Robotics & Automation; Seoul, Korea; May 21-26, 2001; pp. 626-631.

(Continued)

*Primary Examiner* — Rene Towa
(74) *Attorney, Agent, or Firm* — Miles & Stockbridge P.C.

(57) ABSTRACT

In the field of virtual reality, virtual tool manipulation systems and related methods and software are described in the present disclosure. One implementation of a virtual tool manipulation system, among others, comprises a motion tracking system configured to generate motion information related to the position of a part of a user's body. The virtual tool manipulation system also comprises a haptic feedback system configured to provide a haptic sensation to the user based on the motion information, the position of a virtual tool, and characteristics of the virtual tool.

17 Claims, 4 Drawing Sheets

(56) References Cited

U.S. PATENT DOCUMENTS

| | | | |
|---|---|---|---|
| 6,126,450 A * | 10/2000 | Mukai | G09B 23/28 434/262 |
| 6,324,296 B1 * | 11/2001 | McSheery et al. | 382/107 |
| 6,377,011 B1 | 4/2002 | Ben-Ur | |
| 6,421,048 B1 * | 7/2002 | Shih et al. | 345/419 |
| 7,084,884 B1 * | 8/2006 | Nelson | G06F 3/014 345/156 |
| 7,202,851 B2 * | 4/2007 | Cunningham et al. | 345/156 |
| 2002/0133264 A1 * | 9/2002 | Maiteh et al. | 700/182 |
| 2002/0137014 A1 * | 9/2002 | Anderson et al. | 434/262 |
| 2003/0001592 A1 * | 1/2003 | Boronkay | G01D 5/1655 324/699 |
| 2003/0025723 A1 * | 2/2003 | Olien | G09B 23/285 715/701 |
| 2005/0162383 A1 | 7/2005 | Rosenberg | |
| 2005/0202384 A1 * | 9/2005 | DiCuccio | G09B 23/285 434/262 |
| 2005/0203367 A1 * | 9/2005 | Ahmed et al. | 600/407 |
| 2005/0255434 A1 * | 11/2005 | Lok | G09B 23/28 434/262 |
| 2005/0289472 A1 * | 12/2005 | Morita et al. | 715/757 |
| 2006/0084050 A1 * | 4/2006 | Haluck | 434/365 |
| 2006/0190823 A1 * | 8/2006 | Cunningham et al. | 715/701 |
| 2008/0009771 A1 * | 1/2008 | Perry | B25J 9/0006 600/587 |
| 2008/0015418 A1 * | 1/2008 | Jarrell et al. | 600/300 |
| 2008/0058836 A1 * | 3/2008 | Moll | A61B 1/00082 606/130 |

FOREIGN PATENT DOCUMENTS

| | | | |
|---|---|---|---|
| JP | 2000-259074 A | | 9/2000 |
| JP | 2001100879 A | | 4/2001 |
| JP | 2004-318400 A | | 11/2004 |
| WO | 01/18617 A1 | | 3/2001 |

OTHER PUBLICATIONS

Official Communication issued in the corresponding International Application No. PCT/US2008/086008 dated Dec. 17, 2009.

New Virtual Reality Surgery Simulator Hones Surgeons' Skills, Improves Patient Safety, Jun. 20, 2005, Oregon Health & Science University, http://www.ohsu.edu/ohsuedu/newspub/releases/062005virtual.cfm.

Stansfield, Sharon et al., Design and Implementation of a Virtual Reality System and Its Application to Training Medical First Responders, Presence, vol. 9, No. 6, Dec. 2000, pp. 524-556.

Qualter, John et al., 3D Modeling and Animation of the Virtual Surgery Patient, 2005 Slice of Life Conference for Medical Multimedia Developers and Educators, American Association of Medical Colleges; Jun. 14-18, 2005; Portland OR.

CyberForce—Whole Hand and Arm Force Feedback for the CyberGlove, http://www.vrealities.com/cyberforce.html (last visited Dec. 10, 2007).

CyberGlove II—Virtual Reality Glove, http://www.vrealities.com/cyber.html (last visited Dec. 10, 2007).

CyberGrasp—Haptic Interface for the CyberGlove, http://www.vrealities.com/cybergrasp.html (last visited Dec. 10, 2007).

CyberTouch—Force Feedback Option for the CyberGlove, http://www.vrealities.com/cybertouch.html (last visited Dec. 10, 2007).

Doug A. Bowman, 3D user interface, The publishing division of Maruzen Co., Ltd., Sep. 30, 2005, first edition, p. 103-117.

Shigeki Yokoi, "Potential of Surgical Simulation System and Virtual Reality", December number of New Medicine in Japan, Association for Promotion of M E Co., Ltd., Dec. 1, 1992, vol. 19, No. 12.

Kazuhiro Annoura, "The 10th year anniversary DVD-ROM of the Virtual Reality Society of Japan", Proceedings of the Third Virtual Reality Society of Japan Annual Conference, Aug. 19, 1998, p. 83-86.

Japanese Office Action dated Mar. 4, 2014 for corresponding Japanese Patent Application No. 2010-542230 with English translation.

IEEE.org, "Multi-camera hand pose recognition system using skeleton image", IEEE Xplore Digital Library, IEEE Standards, IEEE Spectrum, http://ieeexplore.ieee.org/xpl/login.jsp?tp=&arnumber=531963&url=http%3A%2F%2Fieeexplore.ieee.org%2Fxpls%2Fabs_all.jsp%3Farnumber%3D531963, last downloaded Sep. 12, 2014.

* cited by examiner

VIRTUAL TOOL MANIPULATION SYSTEM

TECHNICAL FIELD

The present disclosure generally relates to virtual reality and more particularly relates to simulating tools that can be manipulated in a virtual environment.

BACKGROUND

During training, an apprentice learns how to use tools associated with a particular trade. Usually, the training process involves the apprentice, under supervision, practicing with the actual tools to conduct a specific action upon a subject. For example, the subject in this respect can be a living organism or an inanimate object, particularly dependent upon the type of tool being used. Tool manipulation skills can be developed, for instance, until the apprentice can become adequately proficient at the trade. Even in the medical field, for example, a medical student or surgeon-in-training learns the skills of handling specialized tools for performing different types of surgical or interventional procedures.

In medical training, the surgeon-in-training typically learns the art of tool handling on a cadaver, animal, or box-type trainer. However, in recent years, systems have been developed that allow a trainee to practice surgical procedures in a virtual environment where no real bodies are needed. In some virtual reality systems, the actual handle of a surgical tool is removed from the rest of the tool. Sensors are then attached to the surface of the handle to detect the position and orientation of the tool in a three-dimensional space. An interface allows the sensors to communicate with a computer and information related to how the handle is manipulated is transferred to the computer for further processing. Images of the tool in a virtual realm are displayed on a visual display device to simulate, in a visual sense, how an actual tool might affect the subject in reality.

One disadvantage of the conventional virtual reality system, in which sensors are attached to the surface of a handle of the tool, is that specific simulation hardware is required for each tool. Thus, it can be very expensive to configure the appropriate sensing hardware and software for a large number of different tools. In order to overcome these and other deficiencies of conventional systems, and to more realistically simulate tool-handling procedures, further improvements can still be made in the field of virtual reality involving the manipulation of tools. Not only can improved systems provide a trainee with more realistic training, but also improvements can be made to provide additional benefits, as well as improved tool design methodologies and rapid prototyping of new instruments.

SUMMARY

The present disclosure describes systems, methods, and associated software applications for simulating virtual tools and for virtually handling the virtual tools. According to one embodiment among many described herein, a virtual tool manipulation system comprises a motion tracking system configured to generate motion information related to the position of a part of a user's body. The virtual tool manipulation system further comprises a haptic feedback system configured to provide a haptic sensation to the user based on the motion information, the position of a virtual tool, and characteristics of the virtual tool.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components in the following figures are not necessarily drawn to scale. Instead, emphasis is placed upon clearly illustrating the general principles of the present disclosure. Reference characters designating corresponding components are repeated as necessary throughout the figures for the sake of consistency and clarity.

DETAILED DESCRIPTION

Figure 1:
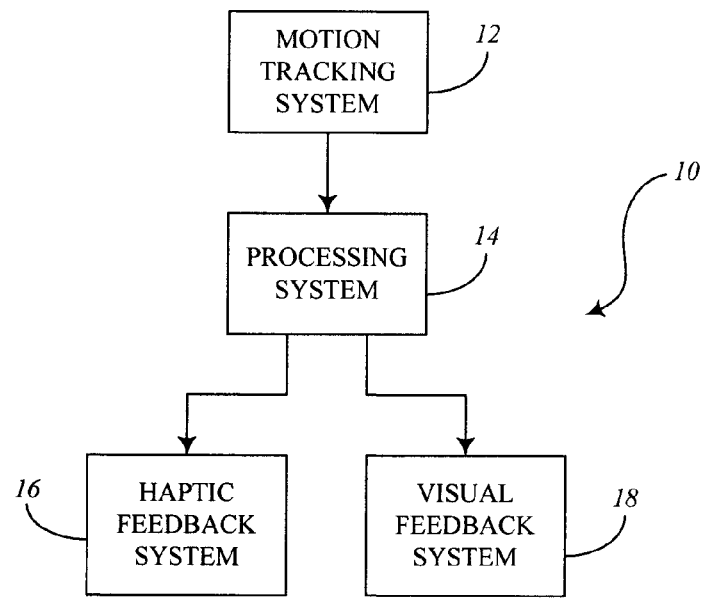
FIG. 1 is a block diagram of a virtual tool manipulation system according to one embodiment.

Virtual training for surgical procedures has provided a means for visually displaying images of what a surgery might actually look like in reality. In conventional systems, the handle of an actual surgical tool is removed from the tool and a number of sensors are placed on the handle to detect the position and orientation of the surgical tool in a virtual realm. However, the cost involved in creating a handle sensor device and associated software for interpreting movement of the device can be very expensive, especially when sensor devices and associated hardware and software is needed for each tool.

The present disclosure provides a lower cost alternative to the conventional systems by allowing any tool design, even new tool designs, to be simulated. More particularly, the design of a tool—either an existing tool or a design of a new tool—can be entered into memory using a computer-aided design (CAD) program. Using the design of a tool in additional to other relevant characteristics of the tool, e.g. weight, weight distribution, center of gravity, degrees of freedom, sharpness, resiliency, etc., the present system can provide haptic or kinesthetic feedback to the user to give the user the sensation of the tool's characteristics, as if the user were actually holding a real tool. The haptic feedback gives the user the sensation of position, movement, tension, etc. of the virtual tool.

By simulating the tool in the virtual world, there is no need to actually manufacture a prototype of the tool during design development. According to the teachings of the present disclosure, the user can experience in the virtual world how a tool functions and how it can be handled, while receiving feedback confirming the user's control of the virtual tool. With the ability to simulate tools in this way, a plurality of different types and designs of tools can be simulated and stored. The simulated virtual tools can have different handles, different sizes, shapes, forms, textures, etc. Also, depending on the type of tool being simulated, the tool can be virtually "gripped" in any suitable manner according to the particular design. As a result of either eliminating the need to manufacture a prototype or dramatically reducing the number of prototypes during the R&D phase, and eliminating the need to create associated sensing devices and software for each individual tool, the cost of including numerous tools in a training environment can be greatly reduced compared to systems in which sensing structure and related software for each physical tool must be configured.

Regarding new tool design according to the present disclosure, designs of tools can be entered into a computer and virtually manipulated. With haptic feedback provided to the user, the user is able to experience the sensation of actually holding the tool. Based on the ease of use and the feel of the tool for accomplishing its intended purpose, the design of the tool can then be altered as necessary without the need to manufacture the tool from inception. In this sense, since no physical material is needed, example embodiments described herein can avoid wasting manufacturing and material costs. The iterative process of designing a tool, utilizing the tool in the virtual realm, and tweaking the design of the tool, can result in a better tool design and can be accomplished in a shorter amount of time.

FIG. 1 is a block diagram of an embodiment of a virtual tool manipulation system 10. In this embodiment, virtual tool manipulation system 10 includes a motion tracking system 12, a processing system 14, a haptic feedback system 16, and a visual feedback system 18. In some embodiments, virtual tool manipulation system 10 may also include an audio feedback system (not shown) to provide audio to the user, if desired. For instance, audio feedback may be beneficial to enhance the virtual experience, especially for tools having parts that produce certain sounds, e.g. motors, joint movement, friction, vibration, activation of an instrument, etc.

Virtual tool manipulation system 10, according to the teachings herein, can be configured for simulating any type of operation involving human movement, e.g. computer gaming, surgery, and involving any occupation, e.g. surgeon, aircraft pilot, astronaut, scientist, construction worker, factory worker, etc. Virtual tool manipulation system 10 can be used for training purposes to allow a specialist to practice a procedure in a safe training setting.

Motion tracking system 12 may include sensing devices for tracking the kinematics or position of certain points in three-dimensional space over time. The sensing device can also track the position or angle of these points with respect to each other, or using other motion tracking techniques. In particular, motion tracking system 12 is capable of making several measurements of position every second to simulate continual movement. In some embodiments, motion tracking system 12 does not include a corresponding physical element that the user can hold or touch in reality. Instead, in this case, the virtual tool exists only in the virtual realm and is completely virtual. In other embodiments, motion tracking system 12 includes a physical prop that the user can touch. The physical prop in this case can be, for example, a handle having the approximate size and shape as the virtual tool.

Motion tracking system 12, for example, may include a data glove, such as a CyberGlove™, which can be worn on the hand of a user. The data glove can include sensors for measuring the bending angles of several joints of the user's hand, wrist, and fingers. In some implementations, motion tracking system 12 may be capable of measuring x, y, and z positions in three-dimensional space with respect to a reference point and may further be capable of measuring orientation in space relative to a fixed reference frame. In other embodiments, motion tracking system 12 may include an optical motion capture device for tracking images of the user and calculating the positions and orientations of various user body parts, such as the hand or hands of a user, wrists, arms, shoulders, head, legs, feet, etc., if necessary.

Figure 3:
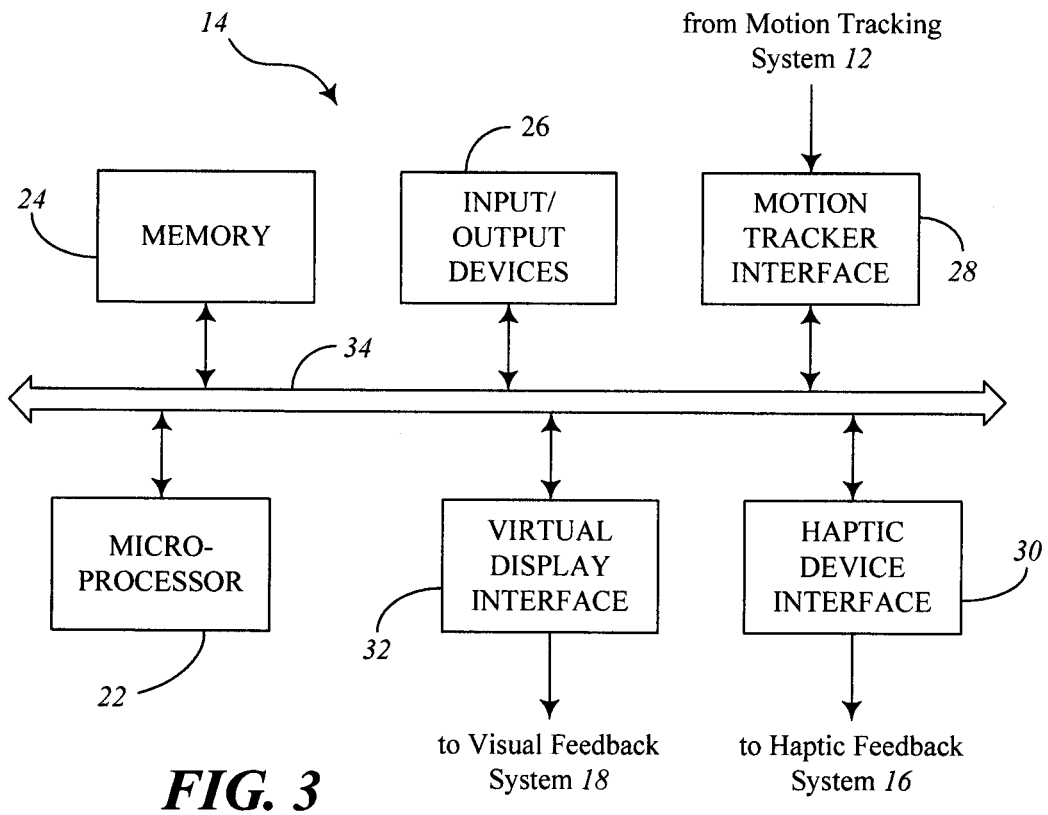
FIG. 3 is a block diagram of the processing system shown in FIG. 1 according to one embodiment.

Processing system 14 may include any suitable processing and storage components for managing the motion information measured by motion tracking system 12. FIG. 3 depicts processing system 14 according to one embodiment, as described in more detail below. Using specific software applications, processing system 14 can analyze the motion information to determine how the user's motion corresponds to a human manipulator in the virtual world. The movement of the human manipulator with respect to virtual tools stored in processing system 14 can be determined. As the human manipulator manipulates the virtual tool, the processing system 14 can also determine the result of an interaction between the virtual tool and a virtual subject. Based on calculations of the interaction between the manipulator and the virtual tool, processing system 14 calculates haptic feedback signals to be applied to haptic feedback system 16. Also, processing system 14 calculates video signals that are applied to visual feedback system 18 to display to the user the virtual image of the interactions among the virtual manipulator, virtual tool, and virtual subject.

Haptic feedback system 16 may include any suitable device that provides any type of forced feedback, vibrotactile feedback, and/or tactile feedback to the user. This feedback is able to provide the user with the sensation of actually holding the simulated tool. Haptic feedback system 16 simulates the physical texture, pressures, forces, resistance, vibration, etc. of the tool, which can be related in some respects to responses to the tool's movement in space and including the interaction of the tool with the subject. Haptic feedback system 16 may include mechanisms such as the CyberGrasp™, CyberForce™, CyberTouch™, etc., for example, which can apply at least the sensations of force, weight, resistance, and vibration to the user.

Visual feedback system 18 may include any suitable virtual reality display device, such as virtual goggles, display screens, etc. Visual feedback system 18 can show the appearance of the tool and how the tool performs when handled by the virtual manipulator. Visual feedback system 18 may also show how the tool reacts to various forces or actions applied to the tool, and how the subject is affected by the virtual tool's movements or operations.

Generally, virtual tool manipulation system 10 operates as follows. Motion tracking system 12 tracks the motion of one or more parts, e.g. hands, of a user's body. The motion information is sent to processing system 14, which processes the motion information and determines how the motion affects a virtual tool. Also, processing system 14 determines how the virtual tool interacts with a particular subject. In response to these processing procedures, processing system 14 provides haptic feedback signals to haptic feedback system 16 based on interactions between the user and the virtual tool depending on the particular motion of the user and characteristics of the virtual tool. Also, processing system 14 provides virtual reality information to visual feedback system 18 to provide real-time visual simulation of the user's hand, tool being manipulated, and the effect of the tool's movement on the subject. In addition, processing system 14 may also create audio signals related to the interactions among the virtual manipulator, virtual tool, and virtual subject.

Figure 2:
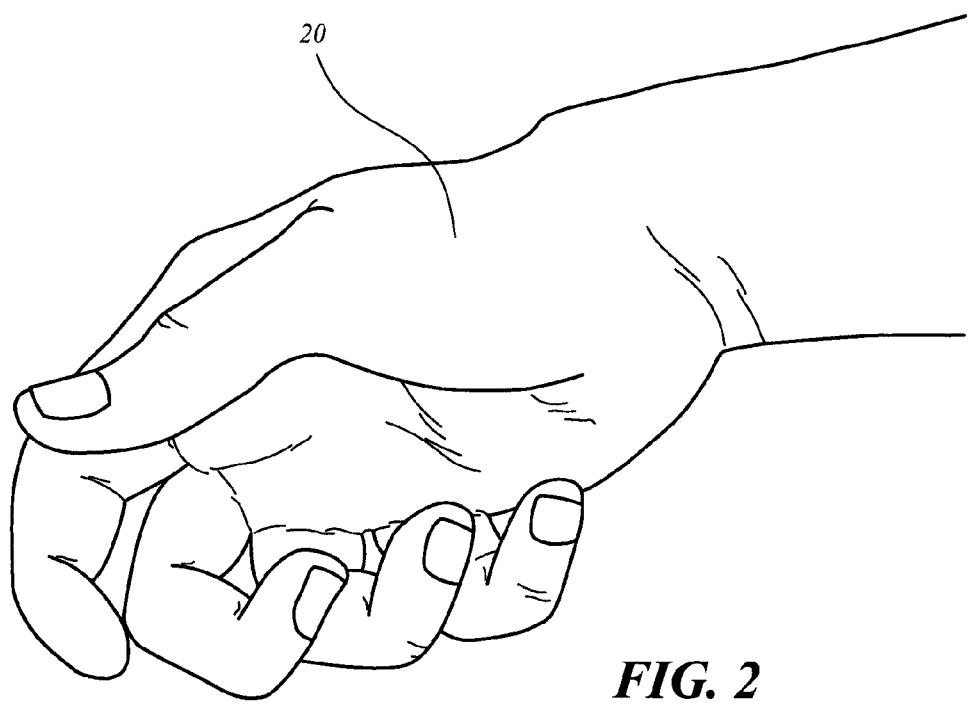
FIG. 2 is an illustration showing a view of a human hand positioned to grip a virtual tool.

FIG. 2 illustrates a view of a real human hand of a user 20 who is using virtual tool manipulation system 10 of FIG. 1. In this view, user 20 has his or her hand positioned in a "Palmar" grip or "dinner knife" grip, which may be used for handling certain tools, e.g. scalpels, lancets, etc. In other embodiments, the hand of user 20 could be positioned in another grip, e.g. a pencil grip, depending on the type of virtual tool being handled. User 20 can represent any human practicing or training in the use of tools or other manipulatable objects. User 20 can be, for example, a surgeon, medical student, pilot in training, scientist, astronaut in training, construction worker, machine operator, factory worker, etc. In the medical field, for example, the tools that may be virtually gripped by user 20 may include forceps, clamps, scalpels, lancets, trocars, retractors, dermatomes, endoscopes, laparoscopic tools, etc. Depending on the particular field, user 20 may virtually manipulate other types of tools.

In some embodiments, user 20 does not actually grasp an actual tool or even a handle of an actual tool, which is unlike conventional systems that normally require the use of a tool handle altered to include sensors thereon. In other embodiments, user 20 may grasp a physical prop that resembles the size and/or shape of an actual tool handle. Although not specifically shown in this figure, motion tracking system 12 (FIG. 1) tracks the motion of user 20 to determine the positioning of the hand, fingers, thumbs, wrist, etc. In some embodiments, motion tracking system 12 may include a data glove, such as a CyberGlove™ or CyberForce™ for sensing positional and/or rotational characteristics of the hand of user 20. In many embodiments, tool manipulation involves a human's hand, but, in other implementations, both hands may be used or even other parts of the human, such as the wrists, arms, head, legs, feet, etc. For example, the positioning of the head of the human can be tracked to determine the angle and line of sight of the human's eyes upon the virtual scene, thereby affecting how the visual signals are displayed by visual feedback system 18.

Also, although not specifically shown, user 20 and/or a data glove worn on the hand of user 20 can receive haptic feedback from haptic feedback system 16 (FIG. 1). For example, haptic feedback system 16 may include any suitable force feedback mechanisms, such as the CyberGrasp™, CyberForce™, CyberTouch™, etc., which can operate in conjunction with a data glove. Particularly, haptic feedback system 16 may include various actuators for simulating the feel of the virtual tool as if it were an actual tool. Also, based on other characteristics of the virtual tool, such as weight, resilience, degrees of freedom, etc., haptic feedback system 16 can provide the sensation of manipulating the virtual tool and provide sensory feedback based on how the tool interacts with the subject. Therefore, haptic feedback system 16, depending on the type of tool is being simulated, can provide the sensation of pressure, forces, tendency to resist movement, gravity, vibration, inertia, etc.

FIG. 3 is a block diagram of an embodiment of processing system 14 shown in FIG. 1. In this embodiment, processing system 14 includes a microprocessor 22, memory 24, input/output devices 26, motion tracker interface 28, haptic device interface 30, virtual display interface 32, each interconnected by an internal bus 34 or other suitable communication mechanism for communicating information. Processing system 14 may also include other components and/or circuitry associated with processing and computing digital or analog electrical signals. Processing system 14 may be configured as a computer that is capable of processing motion control signals detected from a user and providing feedback to the user to simulate the experience of a virtual encounter.

Microprocessor 22 may be a general-purpose or specific-purpose processor or microcontroller. Memory 24 may include internally fixed storage and/or removable storage media for storing information, data, and/or instructions. The storage within the memory components may include any combination of volatile memory, such as random access memory (RAM), and/or non-volatile memory, such as read only memory (ROM). Memory 24 can also store a software program enabling microprocessor 22 to execute a virtual tool manipulation program or procedure. Various logical instructions or commands may be included in the software program for analyzing the user's movements and regulating feedback to the user based on the virtual interactions among the virtual human manipulator, the virtual tool, and the virtual subject. The virtual tool manipulation program of the present disclosure can be implemented in hardware, software, firmware, or a combination thereof. When implemented in software or firmware, the virtual tool manipulation program can be stored in memory 24 and executed by microprocessor 22. When implemented in hardware, the virtual tool manipulation program can be implemented, for example, using discrete logic circuitry, an application specific integrated circuit (ASIC), a programmable gate array (PGA), a field programmable gate array (FPGA), etc., or any combination thereof.

In the embodiment of FIG. 3, memory 24 is illustrated as being part of processing system 14. In other embodiments, parts or all of the memory components associated with processing system 14 may be configured in other processing systems or incorporated on a removable storage device. Also, memory 24 may also include remote storage that is accessible via a modem or other network communication device.

Memory 24 includes files that include information for simulating various portions of the virtual tool environment. For example, the simulation files may include a simulation of the tool itself, a simulation of the manipulator of the virtual tool, and a simulation of the subject that is impacted by the tool's operation. Memory 24 can also include software programs or code for defining how the virtual tool interacts with other things. For example, the interaction between the manipulator and tool as well as the interaction between the tool and the subject can be defined.

Input/output (I/O) devices 26 include input mechanisms such as keyboards, keypads, cursor control devices, e.g. computer mice, or other data entry devices. Output devices may include a computer monitor, display device, printer, or other peripheral devices. The I/O devices 26 may also include a device for communicating with a network, such as a modem, for allowing access to the network, such as the Internet. The I/O devices 26 can communicate with internal bus 34 via wired or wireless transmission.

Motion tracker interface 28 receives information received by motion tracking system 12 (FIG. 1). This information may be stored temporarily or long term in memory 24 and processed to determine the position and/or orientation of user 20. Microprocessor 22 executes the virtual tool manipulation program by analyzing the motion detection information of user 20 and determining the effect of this movement on a virtual tool and the effect of the tool on the virtual subject. Based on these movements and interactions, microprocessor 22 determines feedback signals intended to be applied to user 20. Haptic device interface 30 transfers haptic feedback signals to haptic feedback system 16 to simulate for the user 20 the tactile sensation of handling and controlling the virtual tool. Virtual display interface 32 transfers video signals to visual feedback system 18 to simulate for the user 20 the virtual reality images of the virtual manipulator using the virtual tool on the virtual subject.

Figure 4:
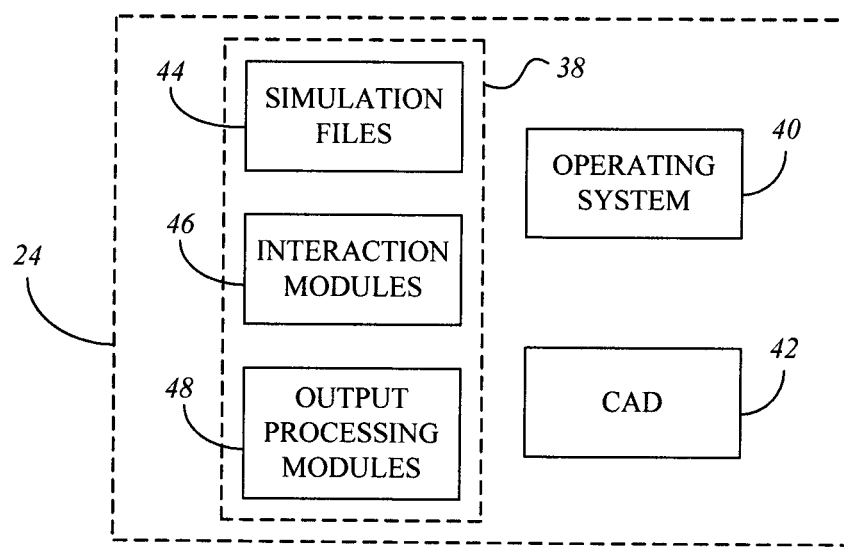
FIG. 4 is a block diagram of the memory shown in FIG. 3 according to one embodiment.

FIG. 4 is a block diagram of an embodiment of memory 24 shown in FIG. 3. In this embodiment, memory 24 includes, among other things, a virtual tool manipulation program 38, an operating system (O/S) 40, and a computer-aided design (CAD) program 42. The virtual tool manipulation program 38 includes, among other things, simulation files 44, interaction modules 46, and output processing modules 48. In some embodiments, memory 24 may include other software applications, such as an Internet browser, word processing program, etc. The CAD program 42 can be installed in memory 24 to enable a tool designer to enter the features of a tool design, which can be stored as the simulation files. Information pertaining to virtual tool manipulator simulation and virtual subject can also be entered using CAD program 42 or other input mechanism. In addition to the tool design, simulation files 44 may also include physical and operational parameters of the tools. In other embodiments, CAD program 42 may be omitted and existing tool design files can be loaded into memory 24 from an external source. Also, tool design files can be downloaded from the Internet and stored in memory 24.

The virtual tool manipulation program 38 manages the simulation of the virtual tool, the simulation of the tool's manipulator, and the subject of the tool's operation, each stored as simulation files 44. The virtual tool manipulation program 38 also manages how the tool interacts with the manipulator and subject, depending on characteristics and properties of the manipulator, tool, and subject defined in simulation files 44. The manner in which they interact can be modeled and defined using software code and stored as interaction modules 46. Output processing modules 48 of virtual tool manipulation program 38 includes software code relating to how information is fed back to the user 20. Based on the virtual interactions of the manipulator, tool, and subject from interaction modules 46, output processing modules 48 provide at least haptic and visual feedback for simulating the virtual tool manipulation experience. Virtual tool manipulation program 38 and any other programs or software code including executable logical instructions as described herein can be embodied in any suitable computer-readable medium for execution by any suitable processing device. The computer-readable medium can include any physical medium that can store the programs or software code for a measurable length of time.

Figure 5:
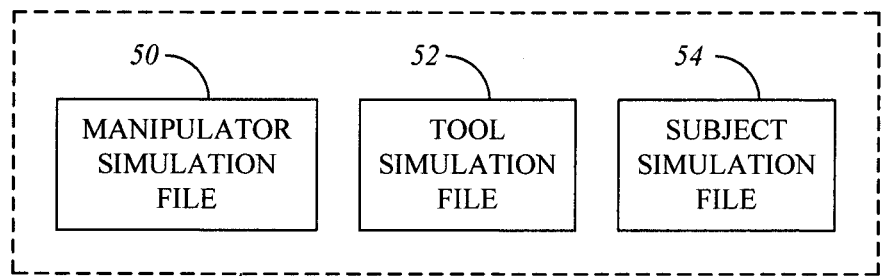
FIG. 5 is a block diagram illustrating the simulation files shown in FIG. 4 according to one embodiment.

FIG. 5 is a block diagram of an embodiment of the simulation files 44 shown in FIG. 4. In this embodiment, the simulation files 44 include a manipulator simulation file 50, a tool simulation file 52, and a subject simulation file 54. Manipulator simulation file 50 includes information defining a virtual human operator. Specifically, since most tools are manipulated by a user's hands, the hands, wrists, and forearms can be simulated with respect to shape, movement, rotation, bending, kinematics, etc. Manipulator simulation file 50 includes various ranges of motion of joints and bones that exist in a human's hand, fingers, wrists, arms, etc. Also included are relative movement information with respect to different joints of a finger and relative movement of one finger with respect to another. Manipulator simulation file 50 can model the human hand and wrist to allow six or more degrees of freedom tracking information to position the virtual hand(s) at any point in the virtual space and oriented at any reasonable angle.

In other embodiments, manipulator simulation file 50 may include other information defining other parts of the human body. For example, if a tool to be simulated involves the manipulator pressing a pedal with his or her foot, then manipulator simulation file 50 includes information regarding various foot positions and orientations. In this respect, manipulator simulation file 50 may include data defining two or more parts of the human body. For some tools, two hands may be needed to utilize the tool properly. In this case, two files, one for each hand, can be modeled. Other implementations of manipulator simulation file 50 can account for variations in the size of the user. For example, the manipulation simulation file 50 may allow modifying the simulation information for a manipulator with large hands, for example.

Tool simulation file 52 stores information or data regarding the parameters, characteristics, and functions of the particular tool being simulated. The information in tool simulation file 52 can be downloaded from an external source or can be produced locally using the CAD program 40. The information includes simulation data of all parts of the virtual tool, including the manipulated parts, e.g. handles, buttons, switches, pulls, etc., and other parts of the structure of the tool, e.g. blades, clamping jaws, tool head, etc. Tool simulation file 52 also includes information regarding the characteristics of the tool, such as size, shape, form, sharpness, texture, force impact, vibration, inertia, center of gravity, weight, weight distribution, degrees of freedom, angles of motion, etc. Other characteristics such as resistance to movement, flexibility, inertia, etc. can also be used to define the tools.

Depending on the type of tool being simulated, tool simulation file 52 may differ significantly from one type to another. For example, virtual surgical tools could include scalpels, lancets, clamps, forceps, retractors, hemostats, dermatomes, endoscopes, laparoscopy tools, etc. Carpentry and construction tool simulated in the tool simulation file may include, for example, hammers, saws, drills, picks, crowbars, etc. Machine operation controls, such as machines for controlling construction equipment, vehicles, factory equipment, etc. can also be simulated and stored as a tool simulation file 52. It should be understood that tool simulation file 52 can include any amount of information for a number of simulated tools. For instance, for surgical training, a surgeon may need certain types of tools for certain procedures. These tools can be stored in related tool simulation files for access as needed. The characteristics of existing tools can be loaded in tool simulation file 52, or, as suggested above, new tools can be designed using appropriate software, such as CAD program 42 (FIG. 4). The physical design as well as the functional design of each of the tools can be stored in tool simulation file 52.

Subject simulation file 54 includes information or data defining the virtual subject that receives the actions of the virtual tool. The subject can be animate or inanimate, depending on the types of tools being simulated. For surgical tools, the subject would normally be animate, such as a human or, in the case of veterinary medicine, an animal. The anatomy and physiology of the human or animal can be modeled and stored in subject simulation file 54. The anatomy may include the body, skin, tissues, organs, bones, muscles, ligaments, tendons, etc. Other parts of the anatomy may also be incorporated in subject simulation file 54 as needed, depending on the type of virtual procedure the user is performing. Subject simulation file 54 may include characteristics of the subject, such as flexibility, strength, resistance to movement, inertia, resilience, ability to be cut or punctured, etc. Also, subject simulation file 54 can be implemented having a range of characteristics as needed. For example, differences in size, shape, age, sex, etc. of a patient can be modeled to better match the type of surgical procedure with an appropriate body type.

In some embodiments, a model can be adapted or derived from CAT scans, CT scans, x-rays, etc. of a specific patient to simulate a virtual representation of the patient to be operated on. In this sense, a surgeon could practice a surgical procedure on the virtual patient to better understand the real conditions of the patient and any risks or complications that may be involved. Also, subject simulation file 54 can include the differences in anatomy between a male patient and female patient if applicable to the particular surgical procedure.

In the fields of building construction or machine operation, the tools would normally be used on inanimate objects, such as lumber, drywall, beams, girders, nails, screws, rivets, or other building materials. Other subjects may include earth, dirt, rocks, concrete, etc. The characteristics of the subjects can be modeled to define the subject's size, shape, weight, flexibility, etc. In other fields in which virtual tools can be simulated and manipulated in a virtual world, other specific subjects receiving the action of the tools can be simulated to reflect a similar subject in reality.

Figure 6:
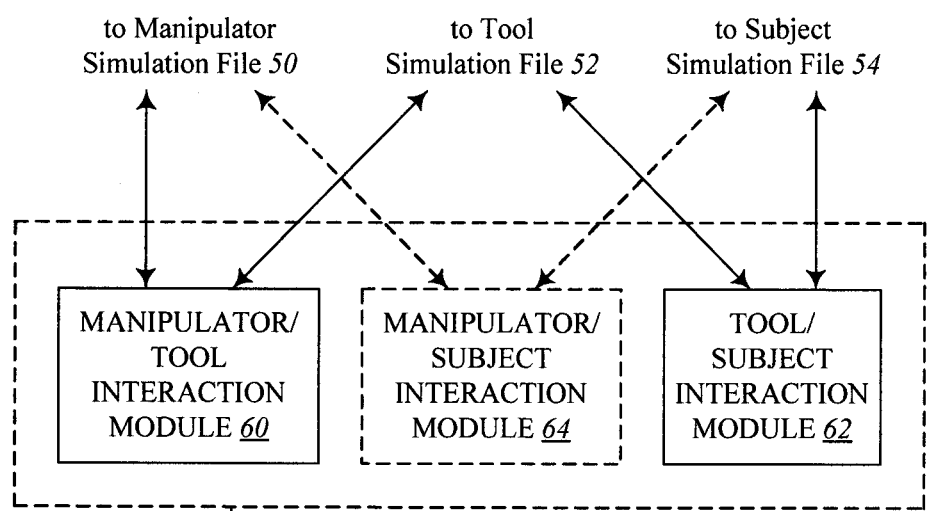
FIG. 6 is a block diagram illustrating the interaction modules shown in FIG. 4 according to one embodiment.

FIG. 6 is a block diagram of an embodiment of interaction modules 46 shown in FIG. 4. In this embodiment, interaction modules 46 include a manipulator/tool interaction module 60 and a tool/subject interaction module 62. In some embodiments, the interaction modules 44 may also include a manipulator/subject interaction module 64, if the condition may apply in which the manipulator actually contacts the subject. Manipulator/subject interaction module 64 may help to simulate a real environment in which the manipulator can directly sense the subject to perceive an understanding of the position of the subject with respect to another hand that may be holding the tool.

Manipulator/tool interaction module 60 includes software programs or code for defining how the manipulator and tool interact with each other. Manipulator/tool interaction module 60 retrieves information from the manipulator simulator file 50 and tool simulation file 52 to determine the characteristics of each. Based on the movements of the manipulator and the characteristics of the tool, manipulator/tool interaction module 60 determines how the tool will move in the virtual realm and what types of haptic feedback the tool might provide to the manipulator. If a tool is grasped in an awkward manner, the haptic feedback can be helpful to the user in that it can be sensed whether or not the grip needs to be corrected. Also, the user might be able to better understand the feel of a tool from the haptic feedback. Also, depending on the flexibility of the manipulator with respect to the tool, certain forces or pressures may be determined to simulate the actual sensation of handling the tool. The movement and orientation of the tool depend on the forces applied by the manipulator and may also react to other forces such as gravity and inertia.

Tool/subject interaction module 62 includes software programs and/or code for defining how the tool and the subject interact with each other. Tool/subject interaction module 62 retrieves information from tool simulation file 52 and subject simulation file 54 to determine the characteristics of each. The interaction of the tool and subject may be based, for example, on the position, orientation, and movement of the tool. Also, based on the strength and other characteristics of the subject, the tool may experience some resistance in its movement. In some situations, this resistance can be applied to manipulator/tool interaction module 60 to translate this resistance to the manipulator. If this is the case, the manipulator may be required to apply additional force or change his or her movement as needed. The reaction of the subject to certain tool functions is also determined by tool/subject interaction module 62. For instance, when the subject is a virtual surgery patient, the use of a tool may result in bleeding or other reactions dependent upon the type of procedure performed on the subject and the portion of the subject encountering the effects of the tool. In a virtual construction setting, the subject may be virtual wood, for example, and the virtual tool may create virtual sawdust as a result of the tool interaction with the wood. These and other interactions between the tool and the subject can be programmed into tool/subject interaction module 62 to simulate a realistic reaction of the subject to the tool and any feedback that the subject may impose on the tool.

Figure 7:
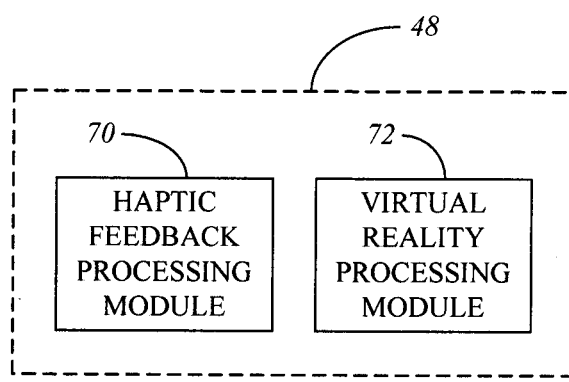
FIG. 7 is a block diagram illustrating the output processing modules shown in FIG. 4 according to one embodiment.

FIG. 7 is a block diagram of an embodiment of the output processing modules 46 shown in FIG. 4. In this embodiment, the output processing modules 46 include a haptic feedback processing module 70 and an audio/video processing module 72. For the embodiments in which virtual tool manipulation system 10 includes the optional audio feedback system for providing an audio feature, the output processing modules 46 may include an audio processing module. In this respect, the audio processing module can generate sound effects based on the various interactions among the manipulator, tool, and subject.

As a result of determining the interactions among the manipulator, tool, and subject, haptic feedback processing module 70 can provide feedback of certain forces, pressures, vibrations, etc. to the manipulator. Not only does haptic feedback processing module 70 derive haptic signals from manipulator/tool interaction module 60 and manipulator/subject interaction module 64, but also haptic feedback processing module 70 can derive indirect haptic signals from tool/subject interaction module 62 that may result from the interaction between the tool and the subject. Haptic signal processed in haptic feedback processing module 70 can be transmitted to haptic feedback system 16 (FIG. 1) via haptic device interface 30 (FIG. 3). Based on the type of haptic feedback system 16 in use, haptic feedback processing module 70 alters the haptic signals to enable haptic feedback system 16 to provide appropriate feedback to the user.

The output processing modules 46 also include the video processing module 72, which generates the virtual reality video image signals. The video processing module 72 may include a graphics processing device for rendering the objects in the three-dimensional virtual world to a two-dimensional display screen. The video image signals generated by the video processing module 72 are transmitted to visual feedback system 18 (FIG. 1) via virtual display interface 32 (FIG. 3).

Figure 8:
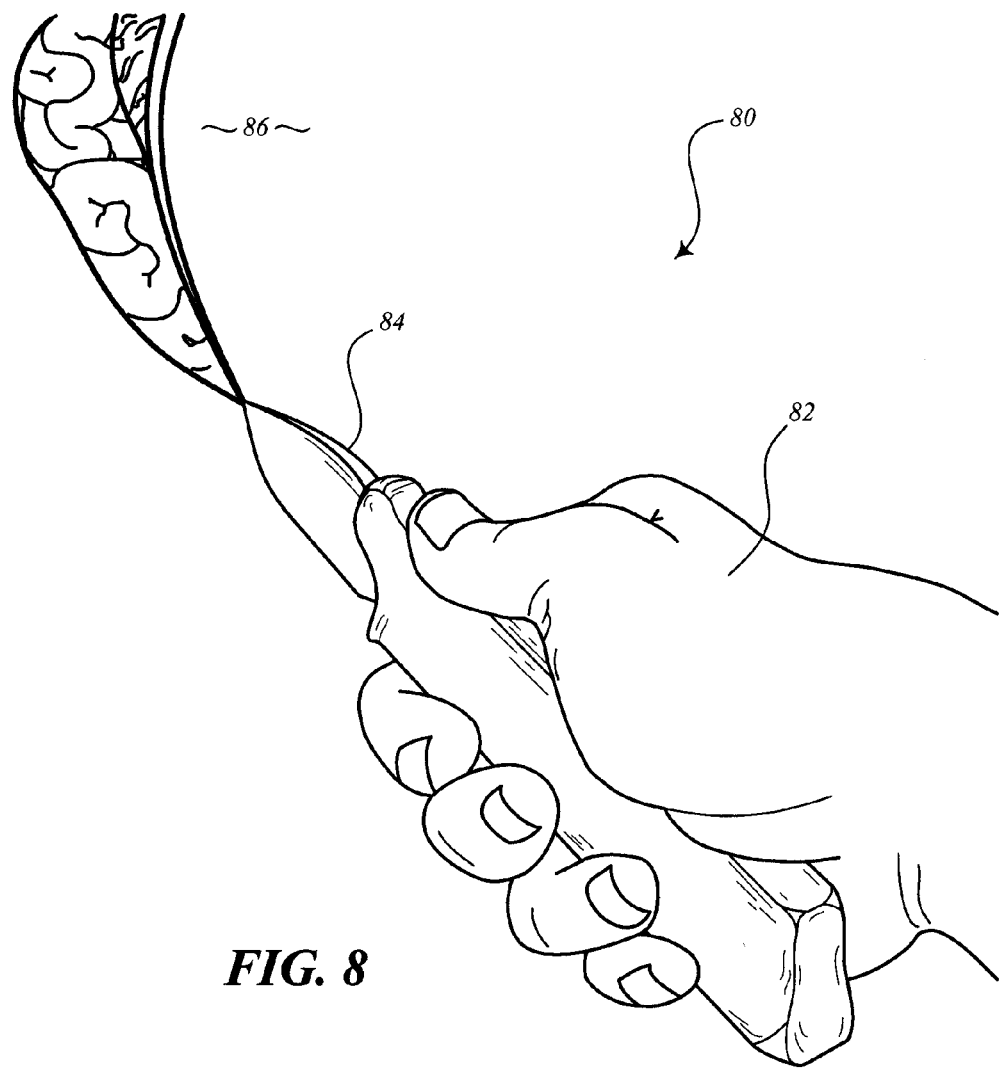
FIG. 8 is an illustration showing a virtual image presented by the visual feedback system shown in FIG. 1.

FIG. 8 illustrates a snapshot of a real-time virtual view 80 in accordance with one example. This virtual view 80 includes images of a virtual manipulator 82, a virtual tool 84, and a virtual subject 86. In particular, the virtual manipulator 82 is the human hand of a virtual surgeon. Also, the virtual manipulator 82 is shown handling the virtual tool 84 in such a way to impose the virtual tool 84 on the virtual subject 86. In this example, the virtual subject 86 is the anatomy of a virtual patient. Because of the tool's interaction with the virtual subject 86, the effect of the virtual tool 84 on the virtual patient can be illustrated as well. In this case, the virtual tool 84 is a scalpel used to cut through the skin of the virtual patient.

It should be understood that the steps, processes, or operations described herein may represent any module or code sequence that can be implemented in software or firmware. In this regard, these modules and code sequences can include commands or instructions for executing specific logical steps, processes, or operations within physical components. It should further be understood that one or more of the steps, processes, and/or operations described herein may be executed substantially simultaneously or in a different order than explicitly described, as would be understood by one of ordinary skill in the art.

The embodiments described herein merely represent examples of implementations and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims.

We claim:

1. A virtual tool manipulation system comprising:
    a motion tracking system, including a first glove having a plurality of sensors and a plurality of actuators, a second glove having a plurality of sensors and a plurality of actuators, and an optical motion capture device, configured to generate motion information related to a user in a three dimensional space by measuring first and second hand position and orientation over time using the plurality of sensors in the first and second gloves, respectively, and head position and orientation over time using the optical motion capture device;
    a visual feedback system configured to display a view of a virtual scene to the user based on head position and orientation in the three dimensional space, the virtual scene depicting a first virtual hand, a second virtual hand, a virtual tool, and a virtual subject, the head position and orientation defining an angle and line of sight of the view of the virtual scene, the visual feedback system further configured to change the view of the virtual scene when the optical motion capture device detects a change in the head position or orientation; and
    a haptic feedback system configured to provide a haptic sensation to the user, using the plurality of actuators in the first and second gloves, based on first and second hand position and orientation in the three dimensional space, characteristics of the virtual subject including flexibility, strength and an ability to be cut or punctured, and characteristics of the virtual tool including an ability to cut or puncture the virtual subject, the haptic sensation simulating manipulating the virtual tool using the first hand of the user, interactions between the virtual tool and the first hand of the user, and interactions between the virtual subject and the second hand of the user.

2. The virtual tool manipulation system of claim 1, further comprising a processing system configured to process the motion information to generate haptic feedback signals, the processing system transmitting the haptic feedback signals to the haptic feedback system, wherein the haptic feedback signals are related to the haptic sensation.

3. The virtual tool manipulation system of claim 2, wherein the processing system comprises a microprocessor, a memory, a first interface device, and a second interface device, the first interface device configured to communicate with the motion tracking system and the second interface device configured to communicate with the haptic feedback system.

4. The virtual tool manipulation system of claim 1, wherein the motion tracking system is configured to track a motion of a human in training and the haptic feedback system is configured to provide haptic feedback to the human in training.

5. The virtual tool manipulation system of claim 4, wherein the human in training is a surgeon-in-training, the virtual tool is a virtual surgical tool, and a subject experiencing actions of the virtual surgical tool is a virtual patient.

6. The virtual tool manipulation system of claim 1, further comprising input/output systems allowing a tool designer to enter a tool design of the virtual tool into a memory, wherein, after the user receives the sensation, the virtual tool manipulation system allows for the tool design of the virtual tool to be altered by the tool designer based on feedback from the user relating to virtually manipulating the virtual tool.

7. A processing device comprising:
    a memory device adapted to store a virtual tool manipulation program;
    a microprocessor adapted to execute the virtual tool manipulation program;
    a motion tracker interface adapted to receive motion information, related to a user in a three dimensional space, from a motion capture system including a first glove having a plurality of sensors and a plurality of actuators, a second glove having a plurality of sensors and a plurality of actuators, and an optical motion capture device, the motion information being generated by measuring first and second hand position and orientation over time using the plurality of sensors in the first and second gloves, respectively, and head position and orientation over time using the optical motion capture device;
    a virtual display interface adapted to generate video signals for a visual feedback system, the video signals depicting a view of a virtual scene based on head position and orientation in the three dimensional space, the virtual scene depicting a first virtual hand, a second virtual hand, a virtual tool, and a virtual subject, the head position and orientation defining an angle and line of sight of the view of the virtual scene, the visual feedback system configured to change the view of the virtual scene when the optical motion capture device detects a change in the head position or orientation; and
    a haptic device interface adapted to generate haptic feedback signals for controlling a haptic feedback device;
    wherein the virtual tool manipulation program causes the microprocessor to simulate a surgical procedure and provide a haptic sensation to the user, using the plurality of actuators in the first and second gloves, based on first and second hand position and orientation in the three dimensional space, characteristics of the virtual subject including flexibility, strength and an ability to be cut or punctured, and characteristics of the virtual tool including an ability to cut or puncture the virtual subject, the haptic sensation simulating manipulating the virtual tool with the first hand of the user, interactions between the virtual tool and the first hand of the user, and interactions between a virtual subject and the second virtual hand of the user.

8. The processing device of claim 7, further comprising input/output devices allowing a tool designer to enter a tool design of the virtual tool into the memory device, wherein, after the user receives the sensation, the virtual tool manipulation program allows for the tool design of the virtual tool to be altered by the tool designer based on feedback from the user relating to virtually manipulating the virtual tool.

9. The processing device of claim 7, wherein the virtual tool manipulation program is implemented on a computer-readable medium.

10. The processing device of claim 9, wherein:
the virtual tool manipulation program comprises simulation files, interaction modules, and output processing modules;
the simulation files simulate the first virtual hand, the virtual tool, and the virtual subject;
the interaction modules simulate a first interaction between the first virtual hand and the virtual tool and a second interaction between the virtual tool and the virtual subject; and
the output processing modules generate signals to stimulate at least one sense of the user; and
wherein the at least one sense corresponds to the first interaction and the second interaction.

11. The processing device of claim 10, wherein the output processing modules generate haptic feedback signals and virtual reality image signals.

12. A virtual tool manipulation program stored on a tangible computer-readable medium, the virtual tool manipulation program comprising:
simulation data configured to define characteristics of a virtual tool, a first virtual hand, a second virtual hand, and a virtual subject;
logic configured to define one or more interactions between the virtual tool, the first virtual hand, the second virtual hand, and the virtual subject;
logic configured to receive motion information, related to a user in a three dimensional space, from a motion capture system including a first glove having a plurality of sensors and a plurality of actuators, a second glove having a plurality of sensors and a plurality of actuators, and an optical motion capture device, the motion information being generated by measuring first and second hand position and orientation over time using the plurality of sensors in the first and second gloves, respectively, and head position and orientation over time using the optical motion capture device;
logic configured to generate video signals for a visual feedback system, the video signals depicting a view of a virtual scene based on head position and orientation in the three dimensional space, the virtual scene depicting the first virtual hand, the second virtual hand, the virtual tool, and the virtual subject, the head position and orientation defining an angle and line of sight of the view of the virtual scene, the visual feedback system configured to change the view of the virtual scene when the optical motion capture device detects a change in the head position or orientation; and
logic configured to generate output information for controlling a haptic feedback system to provide a haptic sensation to the user based on first and second hand position and orientation in the three dimensional space, characteristics of the virtual subject including flexibility, strength and an ability to be cut or punctured, and characteristics of the virtual tool including an ability to cut or puncture the virtual subject;
wherein the haptic sensation simulates manipulating the virtual tool using the first hand of the user, interactions between the virtual tool and the first hand of the user, and interactions between the virtual subject and the second hand of the user.

13. The virtual tool manipulation program of claim 12, wherein:
the simulation data defining the virtual tool is configured to define a virtual surgical tool;
the simulation data defining the first virtual hand is configured to define a virtual surgeon; and
the simulation data defining the virtual subject is configured to define a virtual patient.

14. The virtual tool manipulation program of claim 12, wherein the logic configured to define the one or more interactions further comprises a manipulator/tool interaction module for analyzing the interactions between the first virtual hand and the virtual tool and a tool/subject interaction module for analyzing the interactions between the virtual tool and the virtual subject.

15. The virtual tool manipulation program of claim 14, wherein the logic configured to define the one or more interactions further comprises a manipulator/subject interaction module for analyzing the direct interactions between the first virtual hand and the virtual subject.

16. The virtual tool manipulation program of claim 12, wherein the logic configured to generate output information further comprises an audio processing module configured to generate audio signals for providing audio output to the user.

17. The virtual tool manipulation program of claim 12, wherein a tool design of the virtual tool is entered into the simulation data by a tool designer, wherein, after the user receives the sensation, the virtual tool manipulation program allows for the tool design of the virtual tool to be altered by the tool designer based on feedback from the user relating to virtually manipulating the virtual tool.

* * * * *